United States Patent [19]

Martin

[11] 4,356,264

[45] Oct. 26, 1982

[54] ZINC-CONTAINING ANTIBIOTIC AGENTS

[75] Inventor: Jerome L. Martin, Terre Haute, Ind.

[73] Assignee: International Minerals & Chemical Corp., Terre Haute, Ind.

[21] Appl. No.: 139,597

[22] Filed: Apr. 11, 1980

[51] Int. Cl.$^3$ .................. C12P 17/18; A61K 31/555; C12R 1/465

[52] U.S. Cl. .................................... 435/119; 424/245; 435/886

[58] Field of Search ...................... 435/119, 121, 118

[56] References Cited

U.S. PATENT DOCUMENTS

| | | | |
|---|---|---|---|
| 3,873,715 | 3/1975 | Pressman et al. | 424/283 |
| 3,907,832 | 9/1975 | Hamill | 424/283 X |
| 3,923,823 | 12/1975 | Gale et al. | 424/272 X |
| 3,985,893 | 10/1976 | Holland et al. | 424/272 |
| 4,058,620 | 11/1977 | Westley | 424/283 |
| 4,076,834 | 2/1978 | Westley | 424/283 |
| 4,083,968 | 4/1978 | Westley | 424/181 |
| 4,100,171 | 7/1978 | Westley et al. | 424/274 |
| 4,129,578 | 12/1978 | Celmer et al. | 424/283 X |
| 4,129,659 | 12/1978 | Pressman et al. | 424/283 |
| 4,148,890 | 4/1979 | Czok et al. | 424/181 |
| 4,161,520 | 7/1979 | Osborne et al. | 424/115 |
| 4,164,586 | 8/1979 | Westley | 424/283 |
| 4,181,573 | 1/1980 | Westley et al. | 435/119 |

OTHER PUBLICATIONS

Westley, Advances in Applied Microbiology, vol. 22, pp. 177–223 (1977).
Pfeiffer et al., Biochemistry, vol. 15, No. 5, pp. 935–943 (1976).
Pressman, Ann. Rev. Biochemistry, 1976, pp. 501–530.
Liu et al., Journal of Antibiotics (Japan) vol. 32, pp. 95–99 (1979).
Westley et al., Journal of Antibiotics (Japan) vol. 32, pp. 100–107 (1979).

*Primary Examiner*—Lionel M. Shapiro
*Attorney, Agent, or Firm*—H. J. Barnett

[57] ABSTRACT

Zinc complexes of mononitrogen-containing divalent pyrrole ether antibiotics are provided. Such complexes act as coccidiostats and growth-promoting agents when administered to poultry and act as active agents for improving cardiovascular function in animals.

Zinc complexes of the type disclosed can be prepared by adding soluble zinc salt to a fermentation beer containing the mononitrogen-containing pyrrole ether antibiotic to thereby form an insoluble, recoverable biomass containing the desired zinc antibiotic complex.

15 Claims, No Drawings

ZINC-CONTAINING ANTIBIOTIC AGENTS

The present invention relates to zinc complexes of mononitrogen-containing divalent pyrrole ether antibiotics as new compositions of matter. The present invention also relates to methods for producing zinc complexes of mononitrogen-containing divalent pyrrole ether antibiotics. The present invention further relates to processes for the administration of zinc complexes of mononitrogen-containing divalent pyrrole ether antibiotics to poultry to promote poultry growth, to enhance poultry feeding efficiency, and/or to combat coccidial infections in poultry. In addition, the present invention relates to feed compositions and feed additive compositions containing zinc complexes of mononitrogen-containing divalent pyrrole ether antibiotics. The present invention also relates to processes for improving cardiovascular function in animals by administering zinc complexes of mononitrogen-containing divalent pyrrole ether antibiotics. The present invention further relates to pharmaceutical compositions including zinc complexes of mononitrogen-containing divalent pyrrole ether antibiotics for improving cardiovascular function in animals. The present invention also relates to methods for the purification of zinc complexes of mononitrogen-containing divalent pyrrole ether antibiotics which are formed in fermentation beers such that the zinc complexes are more suitable for administration to an animal such as a human being.

The groups of compounds known as polyether antibiotics can be generally characterized as carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this group of antibiotics is set forth in Westley, *Adv. Appl. Microbiolgoy* 22, 177–223 (1977). As is mentioned therein, at least twenty different polyether antibiotics were known at the time the article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyethers antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin. For additional clarity, the polyether antibiotics of this class can be referred to as "linear monovalent polyether antibiotics."

Class 1b of the polyether antibiotics was defined by Westley as monovalent monoglycoside polyether antibiotics. These polyether antibiotics, as the class name suggests, include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures. Included within class 1b are the polyether antibiotics septamycin, dianemycin, A-204, lenoremycin, carriomycin and etheromycin.

Class 2a as defined by Westley is directed to divalent polyether antibiotics. These antibiotics are generally of a generally linear configuration, may contain from about two to about three tetrahydropyran and/or -furan structures, up to about three total ring structures and no nitrogen atoms. Included within class 2a are the antibiotics lasalocid and lysocellin. For clarity, the polyether antibiotics of this class may be referred to as "non-nitrogen containing divalent polyether antibiotics."

Class 2b of the polyether antibiotics is directed to divalent pyrrole ethers and thus, in contrast to the antibiotics of the other classes, the class 2b antibiotics contain one or more nitrogen atoms. Unlike the polyether antibiotics of class 2a, the polyether antibiotics of class 2b may be of either a generally linear or branched configuration and they contain up to five total ring structures, most often about four or five ring structures, with at least one ring structure being a pyrrole type structure.

Class 2b can be further subdivided based on the criteria of chemical structure, among others, into a subclass of mononitrogen-containing divalent pyrrole ether antibiotics and into a subclass of polynitrogen-containing divalent pyrrole ether antibiotics. The polyether antibiotics of the former subclass are characterized, as the subclass name suggests, by containing only one nitrogen atom in the polyether antibiotic molecule. The polyether antibiotics of the latter subclass are characterized by containing at least two nitrogen atoms, e.g. 2, 3, etc., in the polyether antibiotic molecule. Included in the subclass of mononitrogen-containing divalent pyrrole ether antibiotics is the antibiotic X-14547. The subclass of polynitrogen containing divalent pyrrole ether antibiotics includes the antibiotic A-23187 also known as calcimycin.

Many of the mononitrogen-containing divalent pyrrole ether antibiotics have generally heretofore been recovered and employed in the form of their alkali metal or alkaline earth metal salts. In the recovery, the antibiotic or its alkali metal salts are extracted into various organic solvents with subsequent evaporation of the solvents in a multi-step operation. As an example, a recovery procedure for the X-14547 antibiotic is set forth in U.S. Pat. No. 4,100,171 to Westley et al. In the procedure detailed in Example 2 of the patent, a whole fermentation broth containing the X-14547 antibiotic was produced and then an equal volume of ethyl acetate solvent was added. After stirring for one hour, the solvent layer was separated and concentrated to 2 liters under reduced pressure. The concentrated solvent extract was washed with equal volumes of 1 N HCl three times. The solvent was dried over anhydrous Na$_2$SO$_4$ and concentrated to an oil under reduced pressure. The oil was dissolved in diethyl ether and crude pyrrole-2-carboxylic acid crystals were separated by filtration. Recrystalization from ethanol/ether yielded an analytical sample of the X-14547 antibiotic.

The mother liquor was concentrated to an oil under reduced pressure, redissolved in 250 ml of acetonitrile and washed twice with equal volumes of n-hexane. The hexane washes were pooled and extracted with one-half volume of methanol. The methanol extract was pooled with the acetonitrile and the solvent removed under reduced pressure. The oily solid was dissolved in acetonitrile and after cooling to approximately 3° C. overnight crystalline antibiotic X-14547 was recovered upon filtration as a hemihydrate.

The CH$_3$CN mother liquor was concentrated to an oily solid and subjected to chromatography on a hexane slurry packed 600 g silica gel column. The column was eluted with 250 ml of hexane and then a gradient between 1 liter of 2% ethyl acetate in hexane to 1 liter of ethyl acetate/hexane (3:1) and then 500 ml of ethyl acetate. Fractions of 6 ml each were collected and from fraction numbers 100 to 200 subsequent to the solvent being removed under reduced pressure, additional antibiotic X-14547 was recovered.

As is apparent from the above recitation of one example of a known recovery process for a mononitrogen-containing divalent pyrrole ether antibiotic, such processes can be quite complicated and can require the use of relatively large quantities of various organic solvents, at least some of which may be quite expensive. In addition, such solvent recovery processes inevitably will suffer antibiotic yield losses as well as losses of the various organic solvents used in the process. There is thus a continuing need for antibiotic preparation and recovery processes which effectively and efficiently produce mononitrogen-containing divalent pyrrole ether antibiotics in a form suitable for use as feed additives.

In one aspect, the present invention relates to zinc complexes of mononitrogen-containing divalent pyrrole ether antibiotics. In another aspect, the present invention relates to methods for producing zinc complexes mononitrogen-containing divalent pyrrole ether antibiotics. In another aspect, the present invention relates to processes for the administration of zinc complexes of mononitrogen-containing divalent pyrrole ether antibiotics to poultry to promote poultry growth, to enhance poultry feeding efficiency, and/or to combat coccidial infections in poultry. In yet a further aspect, the present invention relates to feed compositions and feed additive compositions containing zinc complexes of mononitrogen-containing divalent pyrrole ether antibiotics. In yet another aspect, the present invention relates to processes for stimulating cardiovascular function in animals by administering zinc complexes of mononitrogen-containing divalent pyrrole ether antibiotics. In a further aspect, the present invention relates to pharmaceutical compositions including zinc complexes of mononitrogen-containing divalent pyrrole ether antibiotics adapted for use in improving cardiovascular function in animals, particularly in mammals. In still another aspect, the present invention relates to methods for the purification of the zinc complexes of a mononitrogen-containing divalent pyrrole ether antibiotics which are formed in fermentation beers so that the zinc complexes are suitable for administration to a patient requiring improvement in cardiovascular function, e.g., myocardial stimulation.

For convenience, the term "pyrrole ether antibiotic" is used hereinafter for the term "mononitrogen-containing divalent pyrrole ether antibiotic." In addition, the terms "zinc complex" or "complex" are used hereinafter as meaning "a zinc complex of a mononitrogen-containing divalent pyrrole ether antibiotic."

In accordance with the present invention, zinc complexes of pyrrole ether antibiotics can be advantageously formed by adding water-soluble zinc salts to the fermentation broth in which such antibiotics have been produced. When formed in a fermentation beer, the formation of these complexes facilitates the recovery of the pyrrole ether antibiotics from the fermentation beer in which the antibiotics can be produced by, among other things, avoiding the necessity of using recovery methods which involve extractions with organic solvents followed by their subsequent purification and reuse. The resulting broth-insoluble zinc complexes of the antibiotics can then be recovered from the broth and employed, for instance, as coccidiostatic, feeding efficiency improving and growth-promoting agents for poultry. Upon further purification of the recovered zinc complexes by suitable methods the zinc complexes may be utilized in stimulating cardiovascular function in animals.

An antibiotic-containing fermentation broth can be prepared in conventional manner by fermenting a nutrient-containing liquid fermentation medium inoculated with a Streptomyces microorganism capable of producing the desired antibiotic. Suitable liquid fermentation media are generally aqueous dispersions containing a source of assimilable nitrogen and carbohydrates. Nitrogen sources for use in the fermentation media herein can include, for example, yeast, yeast-derived products, corn meal, bean meal, e.g., soy bean meal, etc. Carbohydrate sources for use in the fermentation media herein can include, for example, sugar, molasses, corn-steep liquor and the like. The fermentation media can also contain a variety of optional ingredients, if desired, such as for example, pH adjustment agents, buffers, trace minerals, antifoam agents, filter aids, etc.

The antibiotic can be prepared by growing the Streptomyces microorganism is an aerated, agitated, submerged culture with the pH of the broth adjusted to about neutral, i.e., from about 6.5 to 7.5. Fermentation can generally be carried out at slightly elevated temperatures, e.g., between about 25° C. and 35° C. Incubation of the broth can be carried out for a period of several days, e.g., from about 4 to 6 days or longer if it is economically advantageous to do so.

As was mentioned previously, pyrrole ether antibiotics for forming novel zinc complexes in accordance with the present invention include the pyrrole ether antibiotic known under the code designation X-14547. This antibiotic is characterized chemically as α-(R),5(S)-dimethyl-6(R)-1-ethyl-4-[4-(R)-(2)pyrrolylcarbonyl)-1(S)-ethyl-3a(R),4,5(R),7a(R)-tetrahydroindan-5-yl]-1(E), 3(E)-butadienyl-tetrahydropyran-2-acetic acid. The antibiotic is produced by a *Streptomyces sp.* X-14547 microorganism, a culture of which has been deposited under designation number NRRL 8167 at the Northern Research and Development Division, Agricultural Research Service, United States Department of Agriculture, Peoria, Illinois, U.S.A. The X-14547 antibiotic has the following structural formula;

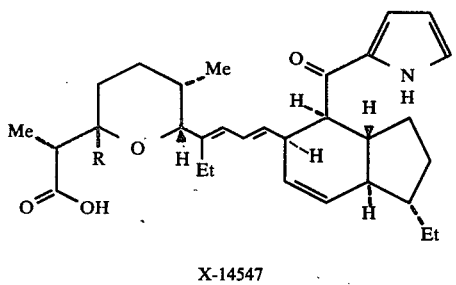

X-14547

Further details of the characteristics of the X-14547 antibiotic and processes for its production and recovery are set forth in U.S. Pat. No. 4,100,171 to Westley et al, in U.S. Pat. No. 4,161,520 to Osborne et al., and in the articles by Liu et al., *J. Antibiotics* 32, 95–99 (1979) and Westley, *J. Antibiotics* 32, 100–107 (1979).

While the above description of a known pyrrole ether antibiotic has identified the antibiotic as being a single compound, it should be recognized that pyrrole ether antibiotics may be produced as an antibiotic complex of structurally related factors containing varying proportions of each factor. It should therefore be realized that the present invention comprehends the zinc complexes of the various factors of the pyrrole ether antibiotics whether in combination with other factors or in their isolated form as well as their use in promoting growth, enhancing feeding efficiency and treating coccidial infections in poultry, and in stimulating cardiovascular function in animals. Furthermore, zinc complexes of derivatives and isomers of the pyrrole ether antibiotics are also within the scope of the present invention. Therefore, as used herein, the specific name of the pyrrole ether antibiotic encompasses all of the factors of the antibiotic, as well as isomers thereof and derivatives thereof.

It is also within the scope of the present invention that the zinc complexes of the pyrrole ether antibiotics can be used in conjunction with other active ingredients which are also useful for challenging coccidial infections in poultry and/or for promoting growth and enhancing feed efficiency in poultry. For example, the zinc complexes of pyrrole ether antibiotics may have an enhanced effect when used in combination with metichlorpindol. Compositions containing certain designated polyether antibiotics and a pleuromutilin derivative which are useful in treating poultry coccidiosis are disclosed in U.S. Pat. No. 4,148,890 to Czok et al.

To the extent necessary, the above-mentioned patents and literature articles mentioned in describing the pyrrole ether antibiotics are incorporated herein by reference.

In accordance with the present invention, the pyrrole ether antibiotic, generally in the form of its alkali metal, alkaline earth metal or ammonium salt, is treated in situ in the fermentation broth or beer by adding to the antibiotic containing broth a water-soluble zinc salt. Addition of such a water-soluble zinc salt promotes the formation of a zinc complex of the pyrrole ether antibiotic. Such a zinc complex of the antibiotic, along with zinc complexes formed with residual nitrogen-containing compounds in the broth such as amino acids, polypeptides, and proteins, are insoluble in the fermentation broth liquid.

The zinc ions from the added zinc salt apparently form coordination bonds with the oxygen atoms of the sparingly soluble antibiotic. On the basis of the formation constants with ligands such as citric acid, lactic acid, and tartaric acid, zinc ions form stronger bonds with oxygen-containing compounds than do ions such as $Mg^{++}$, $Ca^{++}$, $Ba^{++}$, $Na^+$, and $K^+$.

The zinc salt added to the fermentation broth can be various water-soluble salts which ionize in the fermentation broth. Such salts include, for example, zinc chloride, zinc sulfate, zinc acetate, zinc benzoate, zinc citrate, zinc lactate, etc. Water-soluble zinc salts are generally those which can be dissolved to the extent of about 1 percent by weight or more in water at 20° C. For maximum production of the desired zinc complexes, water-soluble zinc salt should be added to the fermented broth in an amount which is sufficient to fill substantially all of the possible zinc coordination sites of the proteins, polypeptides, amino acids and related compounds, in addittion to substantially all of the available coordination sites of the pyrrole ether antibiotic present. Generally, therefore, zinc salt is added to the fermentation broth in an amount sufficient to provide a zinc content of from about 3 to 12 percent and preferably from about 5 to 10 percent by weight of the dried precipitate recovered from the fermentation broth as hereinafter more fully described.

The amount of soluble zinc salt to be added will depend on the amount of nutrients added to the fermentation broth during the course of the fermentation. An actual amount of soluble zinc salt to be added to broth obtained from a given mash bill can be determined by simple laboratory precipitations followed by zinc analyses on the dried precipitates. When, for example, the preferred zinc chloride salt is employed to form the desired zinc antibiotic complex, advantageously from about 4 to 10 gallons of a 67 weight percent zinc chloride solution (sp. gr. 1.883), can be added to 1000 gallons of fermentation broth.

To form the zinc antibiotic complex in the fermentation broth, pH of the broth is advantageously adjusted to about 6.5 to 7.5 and preferably to about 6.8 to 7.2 after addition of the soluble zinc salt to the fermentation broth.

The insoluble zinc complexes formed upon addition of zinc salt can be readily separated from the fermentation broth or beer by conventional filtration or centrifugation techniques. In this manner, a wet biomass, containing the zinc antibiotic complex, is realized. This wet biomass is resistant to wild fermentations because of its relatively high zinc content. The wet biomass so obtained is easily dried by spray drying or drum drying procedures, and this zinc antibiotic-containing dried product can then be used as a feed additive per se. If the antibiotic content of the fermentation beer is lower than desired after completion of the fermentation, crude antibiotic in its alkali metal or alkaline earth metal salt form can be added to the fermentation beer prior to the addition of the soluble zinc salt. In this manner, the antibiotic content of the biomass composition to be separated from the broth can be increased.

Recovery of the zinc antibiotic complexes in the manner described herein provides several important advantages over known antibiotic preparation and recovery processes. The present process, for example, provides a means for recovering relatively high yields of antibiotic in a salable feed additive product. Further, the use of expensive extraction solvents and the cost associated with the process losses of such solvents are avoided. The present process also permits recovery of salable feed values present in the mycelium of the Streptomyces microorganism used to produce the antibiotic. The present process further reduces the cost of waste disposal operations needed in previous processes to deal with the mycelial mat produced during fermentation. Use of this mat as part of the feed additive product, in fact, reduces the cost of the carrier for the antibiotic material being marketed.

The zinc antibiotic complex as hereinbefore described can be added to conventional poultry feed compositions as a coccidiostatic and growth-promoting agent. Such feed compositions generally contain whole or ground cereal or cereal byproducts as an essential nutrient. The feed compositions can also contain such optional additional materials as animal byproducts, e.g., bone meal, fish meal, etc., carbohydrates, vitamins, minerals, and the like. The zinc antibiotic complexes of the present invention are generally employed in the feed compositions to the extent of from about 50 grams per ton to 200 grams per ton, preferably from about 75 grams per ton to 125 grams per ton. A feed additive containing a zinc antibiotic complex of the invention can be used in making the feed composition. The additive preferably contains at least about 5 percent by weight of the zinc antibiotic complex, advantageously from about 10 percent to 50 percent by weight of the zinc antibiotic complex.

As was mentioned previously, the zinc complexes of pyrrole ether antibiotics according to the present invention may also be utilized for the stimulation of cardiovascular functions and particularly in the treatment of ailments such as cardiogenic shock, septic shock and congestive heart failure. Preferably, the zinc complexes are utilized for these purposes in a purified form and are administered either orally or parenterally to a patient requiring treatment. Oral administration is particularly preferred for long term treatment of chronic diseases such as congestive heart failure while parenteral administration is preferred for emergency treatment such as in the treatment of shock and of acute heart failure.

Purification of the zinc complexes so that the complexes are more suitable for administration to humans can be accomplished in a variety of manners. A presently preferred method for purification of the zinc complexes from the recovered feed grade zinc complex includes the steps of, after treatment of the fermentation beer with a soluble zinc salt, acidifying the water slurry of the zinc complex with strong mineral acid such as sulfuric acid to produce a relatively low pH, e.g. a pH below about 4, preferably about 2 to about 3, and then extracting tthe acid form of the pyrrole ether antibiotic from the slurry into a substantially water-insoluble organic solvent such as butyl acetate.

Thereafter, a lower aliphatic alcohol such as methanol is added to the organic solvent containing the pyrrole ether antibiotic. The volume of alcohol added is generally less than or about equal to the volume of organic solvent, preferably about 0.25 to about 1.0 volumes alcohol to about 1.0 volume of organic solvent. A soluble zinc salt such as zinc chloride in the same lower aliphatic alcohol is then slowly added with vigorous agitation to the organic solvent-alcohol mixture containing the pyrrole ether antibiotic so as to form the zinc complex of the pyrrole ether antibiotic. Preferably, about 0.5 to 1.0 volumes of the alcohol containing the zinc salt are added per volume of mixture. The amount of zinc salt added should be sufficient to convert essentially all of the contained antibiotic to its zinc complexed form. The formed zinc complexes are then filtered from the mixture, thoroughly washed, and dried.

If greater purification of the zinc complex is desired, the above procedure can be modified to include further purification steps. One such modification is, prior to the addition of the lower aliphatic alcohol, adding an aqueous solution containing an alkali metal hydroxide such as potassium or sodium hydroxide to the organic solvent containing the pyrrole ether antibiotic so that the antibiotic is extracted into the aqueous solution. The antibiotic is then re-extracted into the same organic solvent or a different water-insoluble organic solvent such as methyl tertiary-butyl ether after acidification. These steps of the modified procedure can be repeated as many times as desired until the proper degree of purification is achieved. Thereafter, the pyrrole ether antibiotic is contacted with the lower aliphatic alcohol and the previously mentioned procedure continued so as to yield the purified zinc complex of the pyrrole ether antibiotic.

In the above description of the purification procedure and modification thereof, the amount of each of the media, i.e., the organic solvent, aliphatic alcohol, aqueous solution, etc., relative to the others when conducting the procedure may vary considerably, the primary considerations being that sufficient media be utilized to obtain a satisfactory yield of the zinc complex balanced against the cost of the media and the capacity of the available equipment. Generally, the amount of a particular medium used to treat another medium in any of the steps of the above procedure is about 0.1 to 10 volumes, preferably about 0.5 to about 5 volumes, for each volume treated.

Certain advantages are realized by the above procedure where the purified zinc complexes are recovered from the feed grade complexes as opposed to recovery of the purified complexes from virgin mycelia. Among others, the feed grade complexes are filtered relatively easily from the fermentation beer whereas filtering of virgin mycelia is very slow and thus time-consuming. In addition, the feed grade complexes tend to be more concentrated and thus less organic solvent is required in conducting the purification procedure and volume loss of solvent will be reduced.

The zinc complexes may be formulated with conventional inert pharmaceutical adjuvant or carrier materials into dosage forms which are suitable for oral or parenteral administration to stimulate cardiovascular function. Such dosage forms include tablets, suspensions, solutions, hard or soft capsules, dragees and the like. The selection of suitable materials which may be used in formulating the active zinc complexes into oral and parenteral dosage forms will be apparent to persons skilled in the art. Such materials, either inorganic or organic in nature, should be of pharmaceutically acceptable quality, free from deleterious impurities and may include, for example, water, dimethylsulfoxide, gelatin albumin, lactose, starch, magnesium stearate, preservatives, stabilizers, wetting agents, emulsifying agents, salts for altering osmotic pressure, buffers, etc. which can be incorporated, if desired, into such formulations.

The quantity of zinc complex which may be present in any of the above described dosage forms generally varies from 10 to 100 mg. per unit dosage. The dosage administered to a particular patient is variable, depending upon the clinician's judgment using the criteria of the condition and size of the patient, the potency of the zinc complex and the patient's particular response thereto. An effective dosage amount of the zinc complex can therefore only be determined by the clinician utilizing his best judgment on the patient's behalf. Generally, parenteral doses should be from about 20 mg. to about 50 mg. for the average size person. Smaller persons or larger persons may require adjustments due to body size. Oral doses, usually capsules, but tablets can be used, generally contain about twice the parenteral dose. The frequency of the administration of the zinc complex depends generally upon the patient's condition and the desired response from the patient. Chronically ill patients may require administration every 2 to 3 hours or once a day, depending on the severity of the disease and the patient's particular response to treatment. Emergency patients generally require only one dose of the zinc complex, particularly those patients in shock.

When administered to a patient requiring treatment, the zinc complexes generally have a positive inotropic effect with little or no chronotropic effects and display minimal, if any, adrenergic action, have a rapid onset of action, require a small effective dose, are non-toxic at the effective doses, have a satisfactory duration of action, display a return to the original pre-drug values of cardiovascular activity, and exhibit continued generally identical responses to subsequently repeated identical dosages.

Illustrated in the following examples are preparation and recovery methods for the zinc complex of the preferred X-14547 antibiotic as well as feed and feed additive compositions including this zinc complex and its usefulness as a coccidiostat and a growth-promoting agent for poultry and, in addition, a pharmaceutical composition including this zinc complex and its usefulness in stimulating cardiovascular function. These examples are in no way to be considered limiting of the present invention to compositions, ingredients, and processes involving that particular antibiotic.

EXAMPLE I

A. Fermentation

About 9.5 liters of fermentation beer containing the X-14547 antibiotic is prepared in accordance with the procedure set forth in Example 1 of U.S. Pat. No. 4,100,171 to Westley. The beer contains at least about 50 mg of the antibiotic per liter.

B. Recovery

To about 2000 ml of fermentation beer, about 12.5 ml of a zinc chloride solution (0.24 g Zn per ml) are slowly added with agitation to the fermentation beer. The pH is adjusted to a value in the range 7.0–7.4. After the treated beer has been agitated for about 30 minutes, it is filtered, without filter aid, on a Buckner funnel using No. 1 Whatman filter paper. The filtration proceeds rapidly to give a firm cake which is dried in an oven. The final dried product contains a significant amount of the zinc complex of the X-14547 antibiotic.

EXAMPLE II

Objective

To determine the efficacy of the zinc X-14547 complex as an anticoccidial compound for poultry, the zinc X-14547 complex is administered to chickens which are challenged by *Eimeria tenella*.

| Test Animals: | | | | | |
|---|---|---|---|---|---|
| Species: | Avian | Total Number: | 24 birds/ treatment | Initial Age: | 14 days |
| Breed: | Hubbard White Mountain | Sex: | Male | Initial Weight: | 330 g |
| Test Materials | Zinc X-14547 - 32.7% pure by weight | | | | |

Test Procedure

1. At 14 days of age chicks are weighed and assigned to groups. Immediately after groups are formed (composed of 12 chicks each) chicks are started on their respective medicated feed ration. Each treatment group is replicated twice for a total of 24 birds per group.

2. Seventy-two hours after the initiation of medication, birds are orally inoculated with approximately 100,000 *Eimeria tenella* oocysts suspended in a 1 cc dose.

3. Controls consist of an infected non-medicated group and a non-infected group.

4. Criteria for evaluation are
    a. Morbidity (4th-6th day)
    b. Mortality (4th-7th day)
    c. Incidence of bloody droppings (4th-6th day)
    d. Body weight gain
    e. Feed per gain
    f. Postmortem lesions.

| | Treatment Groups |
|---|---|
| Pen | Treatment |
| 4, 9 | Zinc X-14547, 75 g/ton |
| 1, 6 | Zinc X-14547, 113 g/ton |
| 5, 7 | Zinc X-14547, 150 g/ton |
| 3, 8 | Non-inoculated control |
| 2, 10 | Inoculated control |

Rations

Rations employed in the Example II testing are summarized in Table 1.

TABLE 1

| Chick Starter (Corn) | | | |
|---|---|---|---|
| % Protein | 23.0 | % Calcium | .98 |
| M.E. Kilocalories/lb | 1376* | % Total phosphorus | .89 |
| Ground yellow corn | | | 55.0 |
| Soybean meal 44% | | | 29.0 |
| Fish solubles | | | 2.0 |
| Meat and bone | | | 5.0 |
| Dehydrated alfalfa meal | | | 1.2 |
| Dried whey | | | 1.0 |
| Animal tallow | | | 4.0 |
| Dicalcium phosphate | | | 1.0 |
| Hubbard super-13 | | | 0.8 |
| Vitamin and trace mineral premix | | | 0.5 |
| Salt | | | 0.5 |
| | | | 100.5 |

*M.E. — Metabolize Energy

Test Results

The results of the administration indicate that a satisfactory challenge is obtained with *E. tenella* and that all three levels of zinc X-14547 demonstrate activity against this organism. In addition, the birds receiving the two lower levels of zinc X-14547 also show superiority over the controls in weight gain and in feed efficiency.

EXAMPLE III

An experiment is conducted to confirm the indication in Example II that zinc X-14547 has growth promoting properties for chickens.

Objective

To determine the efficacy of zinc X-14547 for promoting the growth and improving feed efficiency in broiler chicks.

| Test Animals: | | | | | |
|---|---|---|---|---|---|
| Species: | Avian | Total Number: | 60 birds/ treatment | Initial Age: | 2 days |
| Breed: | Hubbard White Mountain | Sex: | Male | Initial Weight: | 43 g |

Duration of Test: 13 days

Two-day old broiler type chicks are placed into Petersime starter batteries and given feed and water ad libitum for the duration of the test. Chicks are divided into four treatment groups which are replicated six times with ten chicks (males) in each replication. The test period is 13 days. Pen live body weights are taken at 2, 7 and 14 days of age. Pen feed efficiency measurements are taken at 14 days of age.

Rations

Rations employed in the testing are summarized in Table 2.

TABLE 2

| Chick Starter (Rye) | | | |
|---|---|---|---|
| % Protein | 23.2 | % Calcium | 0.98 |
| M.E. Kilocalories/lb | 1260* | % Total phosphorus | 0.89 |
| Ground Rye | | | 55.0 |
| Soybean meal 44% | | | 29.0 |
| Fish solubles | | | 2.0 |
| Meat and bone meal | | | 5.0 |
| Dehydrated alfalfa meal | | | 1.2 |
| Dried Whey | | | 1.0 |
| Animal tallow | | | 4.0 |
| Dicalcium phosphate | | | 1.0 |
| Hubbard Super-13 mineral | | | 0.8 |
| Vitamin and trace mineral premix | | | 0.5 |
| Salt | | | 0.5 |
| | | | 100 lbs |

*M.E. — Metabolizable Energy

Test Results

The results of Example III show that, at levels of 50 and 100 grams per ton, zinc X-14547 improves growth response and feed efficiency of young broiler chicks.

EXAMPLE IV

The zinc complex of X-14547 is purified by a purification process, incorporated into a pharmaceutical composition, and is then administration to dogs to stimulate their cardiovascular function.

Purification

To a liter of fermentation beer slurry containing zinc X-14547 which was produced in a manner as set forth in Example I, sufficient concentrated sulfuric acid is added to acidify the slurry of fermentation beer to a pH of about 3.0. The slurry is then mixed with about one liter of a butyl acetate organic solvent so that the zinc X-14547 is extracted in the solvent. The organic solvent which contains the X-14547 antibiotic is then separated from the acidic aqueous beer and is mixed with about one liter of an aqueous solution of sodium hydroxide having a pH of about 9.0 so that the antibiotic will be extracted into the aqueous alkaline solution. Upon separation of the aqueous alkaline solution from the organic solvent, about one liter of methyl tertiary-butyl ether solvent is added to the aqueous solution to reextract the X-14547 antibiotic into the solvent. Thereafter, about 0.5 liter of methanol is first added to the solvent and then about 0.5 liter of a solution of zinc chloride in methanol is slowly added with vigorous agitation. A zinc complex of X-14547 is thereby formed in the methanol-solvent mixture which is subsequently filtered from the mixture, thoroughly washed with additional methanol and then dried. The formed zinc complex of X-14547 is suitable for administration to stimulate cardiovascular function.

Pharmaceutical Preparation

A pharmaceutical composition containing the zinc complex of X-14547 is prepared, the composition being suitable for parenteral administration.

The following ingredients are utilized to prepare a 5 ml. parenteral solution;

| zinc complex of X-14547 | 50 mg. |
|---|---|
| propylene glycol | 2.5 ml. |
| benzyl alcohol | 0.075 ml. |
| ethyl alcohol | 0.5 ml. |
| water | bal |

Treatment

The above parenteral composition, or any other form of the zinc complexes of the present invention, is administered to animals, e.g. mammals such as, for instance, dogs, prophylactically for, or having, a cardiovascular malfunction to stimulate their respective cardiovascular functions. The procedure utilized is similar to that set forth in U.S. Pat. No. 4,058,620 to Westley. The electrophysical and hemodynamic responses of the dogs are measured before and at various time intervals after intravenous injections of the composition. The parameters measured are myocardial force of contraction, heart rate and blood pressure. Positive inotropic effects are sought with minimal chronotropic effects being manifested in the treated animal.

EXAMPLE V

A zinc complex of X-14547 as purified by the procedure of Example IV is formulated into pharmaceutical tablets suitable for oral administration in stimulating cardiovascular function.

Each tablet has the following composition:

| zinc complex of X-14547 | 25 mg. |
|---|---|
| lactose | 113.5 mg. |
| corn starch | 55.5 mg. |
| pregelatinized corn starch | 8 mg. |
| calcium stearate | 3 mg. |

The tablets are made by thoroughly mixing the zinc complex, lactose, corn starch and pregelatinized corn starch, passing the mixture through a comminuting machine and then moistening the mixture with water in a mixer to produce a paste. The formed paste is screened to form granules and then dried. Calcium stearate is mixed with the dried granules and the granules compressed into tablets using a conventional tableting machine.

While the present invention has been described with reference to particular embodiments thereof, it will be understood that numerous modifications may be made by those skilled in the art without actually departing from the spirit and scope of the invention.

What is claimed is:

1. A method for producing a zinc complex of a mononitrogen containing divalent pyrrole ether antibiotic, said method comprising:
   (a) fermenting a fermentation broth inoculated with a Streptomyces microorganism capable of producing by fermentation of the broth the antibiotic X-14547 for a period of time and under suitable fermentation conditions in order to produce said antibiotic in said fermentation broth;
   (b) providing in said antibiotic containing fermentation broth a water-soluble zinc salt in an amount sufficient to form a zinc complex of X-14547, which complex is insoluble in the fermentation broth; and recovering said insoluble zinc complex of X-14547 from said fermentation broth, wherein the fermentation of the inoculated broth is conducted at a temperature of from about 25° C. to 35° C. and at a pH of from about 6.5 to 7.5.

2. A method in accordance with claim 1 wherein the zinc salt is added to the fermentation broth and is selected from zinc chloride and zinc sulfate.

3. A method in accordance with claim 1 wherein the Streptomyces microorganism employed is *Streptomyces sp.* X-14547.

4. A method in accordance with claim 2 wherein the pH of the fermentation broth is adjusted to within the range of from about 6.5 to 7.5 after said zinc salt is provided in said fermentation broth.

5. A method in accordance with claim 1 wherein the insoluble zinc antibiotic complex is recovered from said fermentation broth as part of a biomass which additionally contains insoluble zinc complexes of residual nitrogen-containing compounds present in the fermentation broth.

6. A method in accordance with claim 5 wherein water soluble zinc salt is added to the fermentation broth in an amount sufficient to provide a zinc content of from about 3 to 12 percent by weight on a dry basis in the biomass recovered from said fermentation broth.

7. A method in accordance with claim 1 further including the steps of:
   (c) acidifying the fermentation broth containing the insoluble zinc complex to form the acidic form of the antibiotic;
   (d) extracting the antibiotic from the broth into a water-insoluble organic solvent;
   (e) adding a lower aliphatic alcohol to the organic solvent containing the antibiotic, the alcohol containing a soluble zinc salt in an amount sufficient to form a zinc complex of the antibiotic; and
   (f) recovering the formed zinc complex of the antibiotic from the organic solvent-alcohol mixture.

8. A method in accordance with claim 7 wherein the aliphatic alcohol is methanol.

9. A method in accordance with claims 7 or 8 wherein the organic solvent is butyl acetate.

10. A method in accordance with claim 7 wherein the fermentation broth is acidified to a pH of 4.0 or less.

11. A method in accordance with claim 7 wherein the zinc salt used in step (e) is zinc chloride.

12. A method in accordance with claim 7 further including the step of adding an aliphatic alcohol to the organic solvent containing the antibiotic prior to step (e).

13. A method in accordance with claim 7 further including the steps of extracting the antibiotic from the organic solvent into an aqueous alkaline solution and then extracting the antibiotic from the aqueous alkaline solution into a second water-insoluble organic solvent.

14. A method in accordance with claim 13 wherein the aqueous alkaline solution contains a metal hydroxide selected from the group consisting of sodium hydroxide and potassium hydroxide.

15. A method in accordance with claim 13 wherein the second water-insoluble organic solvent is selected from the group consisting of butyl acetate and methyl tertiary-butyl ether.

* * * * *